United States Patent [19]

Razdan et al.

[11] 4,036,857
[45] July 19, 1977

[54] BENZOPYRANS HAVING AN UNSATURATED SIDE CHAIN

[75] Inventors: Raj Kumar Razdan, Belmont; Haldean Cloyce Dalzell, Weston, both of Mass.

[73] Assignee: Sharps Associates, Cambridge, Mass.

[21] Appl. No.: 654,158

[22] Filed: Feb. 2, 1976

[51] Int. Cl.$^2$ .................................. C07D 307/83
[52] U.S. Cl. ..................... 260/345.3; 260/240 R; 260/240 J; 424/283; 260/327 M
[58] Field of Search ............ 260/345.3, 240 R, 240 J

[56] References Cited

U.S. PATENT DOCUMENTS

| | | | |
|---|---|---|---|
| 3,856,822 | 12/1974 | Bender et al. | 260/345.3 |
| 3,901,926 | 8/1975 | Winn et al. | 260/345.3 |
| 3,941,782 | 3/1976 | Harris et al. | 260/345.3 |

OTHER PUBLICATIONS

Fahrenholtz, J. Org. Chem., 37, p. 2204 (1972).

*Primary Examiner*—Bernard Helfin
*Assistant Examiner*—Nicky Chan
*Attorney, Agent, or Firm*—Merriam, Marshall, Shapiro & Klose

[57] ABSTRACT

3-Formyl-6a,7,10,10a-tetrahydro-6,6,9-trimethyl-6H-dibenzo[b,d]pyran-1-ol, ethers and esters thereof having the formula

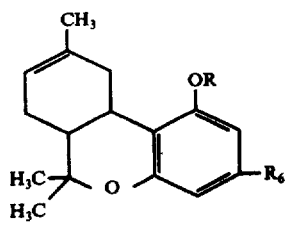

wherein R is hydrogen, lower alkyl or lower alkanoyl and $R_6$ is formyl or 1,3-dithiolan-2-yl but is 1,3-dithiolan-2-yl only when R is hydrogen, and derivatives thereof of the formula

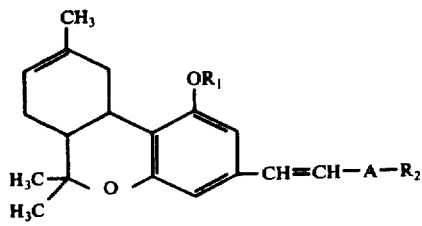

wherein $R_1$ is hydrogen or lower alkanoyl, $R_2$ is alkyl, aryl-lower alkyl or cycloalkyl-lower alkyl, A represents

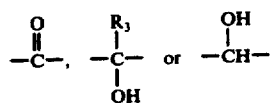

when $R_1$ is hydrogen and $R_3$ is lower alkyl, and A is

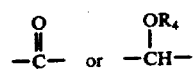

when $R_1$ is lower alkanoyl and $R_4$ is the same lower alkanoyl represented by $R_1$, processes of making such compounds and intermediates useful in such processes, pharmaceutical compositions containing the compounds and the use of the compounds as tranquilizing and antidepressant agents.

12 Claims, No Drawings

BENZOPYRANS HAVING AN UNSATURATED SIDE CHAIN

This invention relates to novel chemical compounds and processes of producing the same. More particularly, this invention is concerned with novel benzopyrans and the use of such compounds, particularly those having pharmacological activity.

According to a first part of the subject invention there is provided the novel 3-formyl-6a,7,10,10a-tetrahydro-6,6,9-trimethyl-6H-dibenzo[b,d]pyran-1-ol, and ethers and esters thereof, of the following formula I:

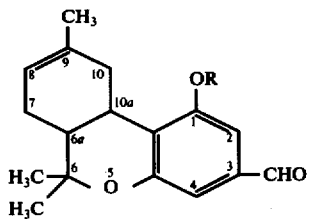

processes of producing such compounds, and novel intermediates used in such processes, wherein R represents hydrogen, lower alkyl or lower alkanoyl groups.

According to a second part of the subject invention there is provided 6a,7,10,10a-tetrahydro-6,6,9-trimethyl-6H-dibenzo[b,d]pyran-1-ols having a 3-substituted alkenyl group, and esters thereof, of the following formula II:

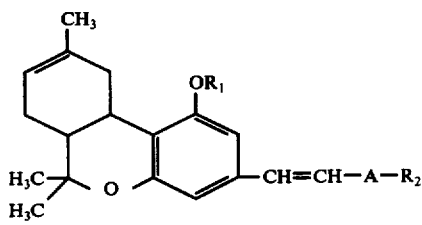

and which are derivatives of compounds of formula I, wherein $R_1$ represents hydrogen or a lower alkanoyl group, $R_2$ is an alkyl, aryl-lower alkyl or cycloalkyl-lower alkyl group and A represents

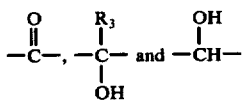

when $R_1$ is hydrogen and wherein $R_3$ is a lower alkyl group, and desirably is methyl or ethyl, and A represents

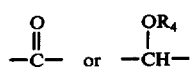

when $R_1$ is a lower alkanoyl group and $R_4$ is the same lower alkanoyl group represented by $R_1$.

As used herein, the term "lower-alkyl" means saturated, monovalent aliphatic radicals, including straight and branched-chain radicals, of from one to six carbon atoms, as illustrated by, but not limited to methyl, ethyl, propyl, isopropyl, butyl, sec.-butyl, amyl and hexyl.

As used herein, the term "alkyl" means saturated, monovalent aliphatic radicals, including straight and branched-chain radicals, of from one to 20 carbon atoms, as illustrated by, but not limited to methyl, n-pentyl, n-hexyl, 2-heptyl, n-heptyl, 1,2-dimethylheptyl, n-octyl, 2-nonyl, 2-tetradecyl, n-hexadecyl and 2-eicosanyl.

As used herein, the term "cycloalkyl" means cyclic, saturated aliphatic radicals having from three to eight carbon atoms, as illustrated by, but not limited to cyclopropyl, cyclobutyl, 2-methylcyclobutyl, cyclohexyl, 4-methylcyclohexyl, cycloheptyl and cyclooctyl.

The term "aryl" includes a single ring, such as phenyl, or a plurality of fully unsaturated rings which can be bonded together or which can be fused rings such as the naphthyl group. In addition, the aryl group can be nuclear substituted with one or more halo groups, such as the chloro and fluoro groups, lower alkyl groups such as methyl and ethyl and lower alkoxy groups such as methoxy and ethoxy.

As used herein, the term "lower-alkanoyl" means saturated, monovalent, aliphatic radicals derived from a monocarboxylic acid, including straight or branched-chain radicals of from one to six carbon atoms, as illustrated by, but not limited to formyl, acetyl, propionyl, α-methyl-propionyl, butyryl and hexanoyl.

Preparation of the Compounds of Formula I

The compounds of formula I in which R is hydrogen can be prepared by reacting a 3,5-dialkanoyloxybenzaldehyde (III) with 1,2-ethanedithiol to produce a 1,3-dialkanoyloxy-5-(1,3-dithiolan-2-yl)benzene (IV), hydrolyzing the 1,3-dialkanoyloxy ester to produce 5-(1,3-dithiolan-2-yl)resorcinol (V), reacting compound V with p-mentha-2,8-dien-1-ol to produce 3-(1,3-dithiolan-2-yl)-6a,7,10,10a-tetrahydro-6,6,9-trimethyl-6H-dibenzo[b,d]pyran-1-ol (VI) which is then subjected to oxidative cleavage conditions to produce a compound of formula I named 3-formyl-6a,7,10,10a-tetrahydro-6,6,9-trimethyl-6H-dibenzo[b,d]pyran-1-ol. This process can be represented as follows:

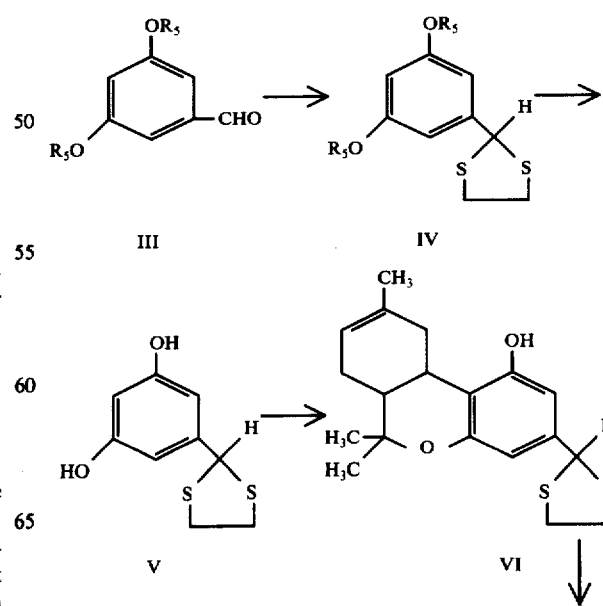

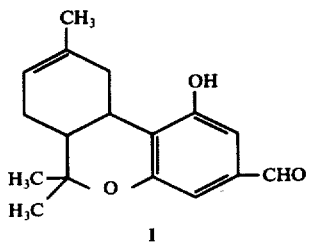

wherein $R_5$ represents a lower alkanoyl group, such as the acetyl, propionyl and butyryl groups.

In the first step of the process a 3,5-dialkanoyloxy-benzaldehyde (III) is reacted with 1,2-ethanedithiol by bringing the reactants together in a suitable inert liquid reaction medium, such as ether or tetrahydrofuran, in the presence of an acid such as hydrogen chloride, sulfuric acid or phosphoric acid to catalyze the reaction and induce formation of the cyclic thioacetal. 3,5-Diacetoxybenzaldehyde [Ber., 74, 869 (1941)] may be used as the starting material. The reaction proceeds at room temperature but can be hastened by moderate heating of the reaction mixture. The desired product can be isolated from the reaction mixture by conventional means, such as evaporating it to dryness. In this way there is obtained a 1,3-dialkanoyloxy-5-(1,3-dithiolan-2-yl)benzene (IV).

In the second step of the process the ester groups of the 1,3-dialkanoyloxy-5-(1,3-dithiolan-2-yl)benzene (IV) are hydrolyzed by use of a strong base, such as solid sodium hydroxide or potassium hydroxide in methanol or some other suitable alkanol. The hydrolysis proceeds to completion quickly. Following acidification of the reaction mixture the desired 5-(1,3-dithiolan-2-yl)resorcinol (V) can be isolated by conventional procedures.

In the third step of the process 5-(1,3-dithiolan-2-yl)resorcinol (V) is reacted with p-mentha-2,8-dien-1-ol having the formula

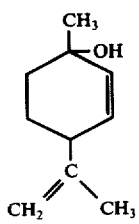

in a suitable liquid reaction medium such as benzene or methylene chloride in the presence of an acid, such as p-toluenesulfonic acid, to induce the condensation. The procedures for this type of reaction are disclosed in Helv. Chim. Acta, 52, 1102 (1969). An elevated temperature, such as the reflux temperature, promotes the reaction and brings it to completion in less than one hour. The desired 3-(1,3-dithiolan-2-yl)-6a,7,10,10a-tetrahydro-6,6,9-trimethyl-6H-dibenzo[b,d]pyran-1-ol (VI) is then obtained from the reaction mixture, and purified, using routine operations.

3-(1,3-dithiolan-2-yl)-6a,7,10,10a-tetrahydro-6,6,9-trimethyl-6H-dibenzo[b,d]pyran-1-ol (VI) in the fourth step is then treated with mercuric oxide and boron trifluoride in an aqueous reaction medium containing an organic solvent which is water miscible, such as tetrahydrofuran. The oxidative cleavage is effected at room temperature to produce 3-formyl-6a,7,10,10a-tetrahydro-6,6,9-trimethyl-6H-dibenzo[b,d]pyran-1-ol which can then be isolated by routine means.

The 3-formyl-6a,7,10,10a-tetrahydro-6,6,9-trimethyl-6H-dibenzo[b,d]pyran-1-ol can be converted to 1-lower alkoxy derivatives by reacting an alkali metal salt of the phenol with a lower alkyl halide in a liquid reaction medium such as benzene or toluene. Some of the ethers which can be produced in this way are the 1-methoxy, 1-ethoxy and 1-propoxy ethers of 3-formyl-6a,7,10,10a-tetrahydro-6,6,9-trimethyl-6H-dibenzo[b,d]pyran.

Lower alkyl esters of 3-formyl-6a,7,10,10a-tetrahydro-6,6,9-trimethyl-6H-dibenzo[b,d]pyran-1-ol are produced by conventional methods by reacting the phenol with a lower alkanoyl halide, lower carboxylic acid, lower carboxylic acid anhydride or other suitable esterifying agent. Representative of the esters which are so produced are the 1-acetoxy, 1-propionyloxy and 1-butyryloxy esters of 3-formyl-6a,7,10,10a-tetrahydro-6,6,9-trimethyl-6H-dibenzo[b,d]pyran.

Preparation of the Compounds of Formula II

The compounds of formula II can be prepared using a phenolic compound of formula I or a lower alkanoyloxy ester thereof as the starting material, by a series of reaction steps which can be illustrated as follows:

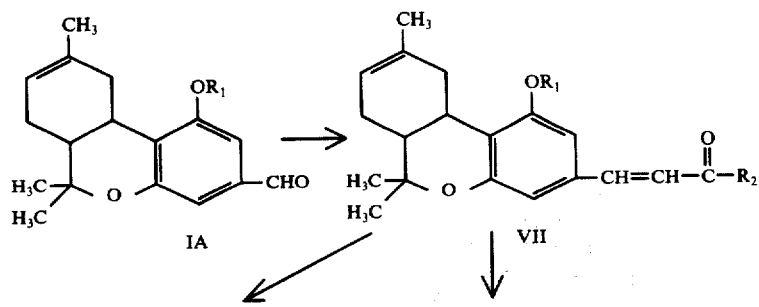

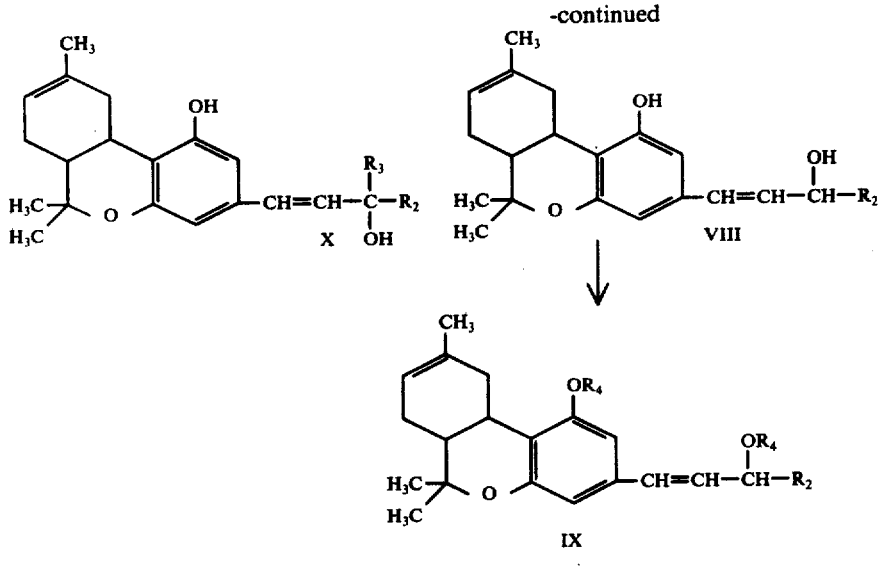

wherein $R_1$, $R_2$, $R_3$ and $R_4$ have the meaning assigned above.

In the first step of the process 3-formyl-6a,7,10,10a-tetrahydro-6,6,9-trimethyl-6H-dibenzo[b,d]pyran-1-ol (IA), or a lower alkanoyloxy ester thereof, is reacted with a dimethyl

phosphonate in the presence of a reactive hydride in a liquid reaction medium to produce a (VII),

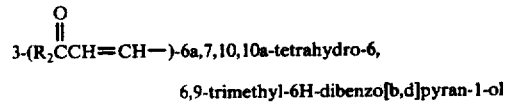

or lower alkanoyloxy ester thereof, using the conditions disclosed in the literature for the Wittig reaction, particularly in G. Wittig, Experienta, 12, 41–48 (1956); Harrison et al., J. Chem. Soc., 1955, 4016; and Organic Reactions, 14, 270–490 (1965).

Among the dimethyl

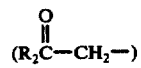

phosphonates which can be used in the process are
dimethyl (2-oxoheptyl) phosphonate,
dimethyl (2-oxobutyl) phosphonate,
dimethyl (2-oxoundecyl) phosphonate,
dimethyl (2-oxo-7-phenylheptyl) phosphonate and
dimethyl (2-oxo-7-cyclohexylheptyl) phosphonate.

Some of the products of formula VII which are produced by the described reaction are
3-(3-oxo-1-octenyl)-6a,7,10,10a-tetrahydro-6,6,9-trimethyl-6H-dibenzo[b,d]pyran-1-ol,
3-(3-oxo-1-pentenyl)-6a,7,10,10a-tetrahydro-6,6,9-trimethyl-6H-dibenzo[b,d]pyran-1-ol,
3-(3-oxo-1-dodecenyl)-6a,7,10,10a-tetrahydro-6,6,9-trimethyl-6H-dibenzo[b,d]pyran-1-ol,
3-[3-oxo-1-(8-phenyl)octenyl]-6a,7,10,10a-tetrahydro-6,6,9-trimethyl-6H-dibenzo[b,d]pyran-1-ol,
3-[3-oxo-1-(8-cyclohexyl)octenyl]-6a,7,10,10a-tetrahydro-6,6,9-trimethyl-6H-dibenzo[b,d]pyran-1-ol
and such compounds in which $R_2$ is methyl, propyl, 1,2-dimethylheptyl, n-hexadecyl, phenylethyl, phenylpentyl, cyclopentylbutyl, cycloheptylhexyl and cyclohexyl-1,2-dimethylheptyl, as well as the lower alkanoyloxy esters, including the acetoxy, propionyloxy and butyryloxy esters, thereof.

The 3-oxo compounds of formula VII can be readily reduced to the 3-hydroxy compounds of formula VIII by the use of a chemical reducing agent suitable for reducing a keto group to an alcohol group without simultaneously reducing an adjoining olefinic unsaturated linkage. When $R_1$ is an alkanoyloxy group the ester may be cleaved in the reduction to form the 1-hydroxy compounds. A chemical reducing agent suitable for the reduction is lithium aluminum hydride in an inert liquid reaction medium such as ether. The desired reduction proceeds rapidly at room temperature. After the reaction is terminated any excess reducing agent may be decomposed by the addition of water and an inorganic base such as sodium hydroxide. The resulting product can then be isolated and purified by conventional procedures. Alternatively, the reduction can be effected using aluminum hydride, diisobutyl aluminum hydride or sodium trimethoxyborohydride in tetrahydrofuran.

Some of the products of formula VIII which are produced by the reduction reactions are
3-(3-hydroxy-1-octenyl)-6a,7,10,10a-tetrahydro-6,6,9-trimethyl-6H-dibenzo[b,d]pyran-1-ol,
3-(3-hydroxy-1-pentenyl)-6a,7,10,10a-tetrahydro-6,6,9-trimethyl-6H-dibenzo[b,d]pyran-1-ol,
3-(3-hydroxy-1-dodecenyl)-6a,7,10,10a-tetrahydro-6,6,9-trimethyl-6H-dibenzo[b,d]pyran-1-ol,
3-[3-hydroxy-1-(8-phenyl)octenyl]-6a,7,10,10a-tetrahydro-6,6,9-trimethyl-6H-dibenzo[b,d]pyran-1-ol,
3-[3-hydroxy-1-(8-cyclohexyl)octenyl]-6a,7,10,10a-tetrahydro-6,6,9-trimethyl-6H-dibenzo[b,d]pyran-1-ol and compounds in which $R_2$ is methyl, propyl, 1,2-dimethylheptyl, n-hexadecyl, phenylethyl, phenylpentyl, cyclopentylbutyl, cycloheptylhexyl and cyclohexyl-1,2-dimethylheptyl.

The di-lower alkanoyloxy esters represented by formula IX can be readily produced by reacting the compounds of formula VIII with a suitable lower alkanoyl halide, lower carboxylic acid, lower carboxylic acid anhydride or other suitable esterifying agent. Some of the reactants which can be used are formic acid, formyl chloride, acetyl chloride, butyryl chloride, acetic anhydride and butyric anhydride. Well known esterification procedures and conditions can be used to make the esters.

Some of the esters of formula IX which can be so produced are 1-acetoxy-3-(3-acetoxy-1-octenyl)-6a,7,10,10a-tetrahydro-6,6,9-trimethyl-6H-dibenzo[b,d]pyran, 1-propionyloxy-3-(3-propionyloxy-1-pentenyl)-6a,7,10,10a-tetrahydro-6,6,9-trimethyl-6H-dibenzo[b,d]pyran, 1-valeroyloxy-3-(3-valeroyloxy-1-dodecenyl)-6a,7,10,10a-tetrahydro-6,6,9-trimethyl-6H-dibenzo[b,d]pyran, 1-acetoxy-3-[3-acetoxy-1-(8-phenyl)octenyl]-6a,7,10,10a-tetrahydro-6,6,9-trimethyl-6H-dibenzo[b,d]pyran and 1-acetoxy-3-[3-acetoxy-1-(8-cyclohexyl)octenyl]-6a,7,10,10a-tetrahydro-6,6,9-trimethyl-6H-dibenzo[b,d]pyran, and such esters in which $R_2$ is methyl, propyl, 1,2-dimethylheptyl, n-hexadecyl, phenylethyl, phenylpentyl, cyclopentylbutyl, cycloheptylhexyl and cyclohexyl-1,2-dimethylheptyl.

The 3-keto compounds of formula VII upon reaction with a lower alkyl Grignard reagent yield the 3-hydroxy-3-lower alkyl tertiary alcohols of formula X. When the lower alkanoyloxy ester of the 3-keto compound is used in the reaction the ester group is cleaved. Some of the Grignard reagents which can be used in the reaction are methyl magnesium bromide, ethyl magnesium bromide, propyl magnesium bromide and butyl magnesium bromide. The reaction is readily effected in an inert liquid reaction medium such as diethyl ether following which the intermediate complex may be decomposed with methanol to give the desired tertiary alcohol. Alternatively, an alkyl lithium such as methyl lithium can be used to produce the compounds of formula X from the compounds of formula VII.

Some of the compounds of formula X which can be produced as described are 3-(3-hydroxy-3-methyl-1-octenyl)-6a,7,10,10a-tetrahydro-6,6,9-trimethyl-6H-dibenzo[b,d]pyran-1-ol, 3-(3-ethyl-3-hydroxy-1-pentenyl)-6a,7,10,10a-tetrahydro-6,6,9-trimethyl-6H-dibenzo[b,d]pyran-1-ol, 3-(3-hydroxy-3-propyl-1-dodecenyl)-6a,7,10,10a-tetrahydro-6,6,9-trimethyl-6H-dibenzo[b,d]pyran-1-ol, 3-[3-hydroxy-3-methyl-(8-phenyl)octenyl]-6a,7,10,10a-tetrahydro-6,6,9-trimethyl-6H-dibenzo[b,d]pyran-1-ol, and 3-[3-ethyl-3-hydroxy-1-(8-cyclohexyl)octenyl]-6a,7,10,10a-tetrahydro-6,6,9-trimethyl-6H-dibenzo[b,d]pyran-1-ol and otherwise identical compounds but with $R_2$ of formula X being methyl, propyl, 1,2-dimethylheptyl, n-hexadecyl, phenylethyl, phenylpentyl, cyclopentylbutyl, cycloheptylhexyl and cyclohexyl-1,2-dimethylheptyl.

If desired, the compounds of formula X can be diesterified, in the same way the esters of formula IX are produced from the compounds of formula VIII. Due to the greater reactivity of the phenolic hydroxy as compared to the tertiary alcohol, and depending on the reaction conditions chosen, either the mono or the diesters can be formed. Typical esters of compounds of formula X, such as those specifically named herein, which may be so produced are the acetoxy, propionyloxy and valeroyloxy esters.

An additional method of producing the compounds of formula VII is to use the Claisen-Schmidt condensation and react a compound of formula IA with a methyl-$R_2$-ketone. This process can be illustrated as follows:

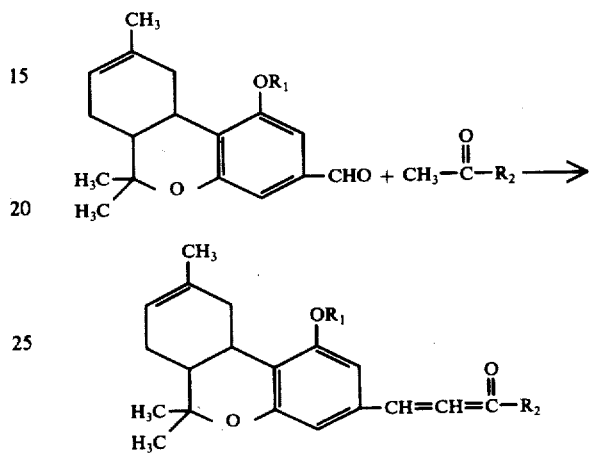

The reaction proceeds readily by combining the reactants in a suitable liquid reaction medium containing a small amount of a strong base such as sodium hydroxide or potassium hydroxide.

Some of the methyl-$R_2$-ketones which can be used in the process are those in which $R_2$ is an alkyl, aryl-lower alkyl or cycloalkyl-lower alkyl as previously named herein.

Pharmaceutical Uses and Compositions

The compounds of formula I are useful intermediates in producing many useful compounds, including the compounds of formula II, because of the reactive 3-formyl group.

The compounds of formulas I and VII to X have tranquilizing activity in animals and such activity indicates potential human use of these compounds as drugs. The compounds also have antidepressant activity.

The compound 3-formyl-6a,7,10,10a-tetrahydro-6,6,9-trimethyl-6H-dibenzo[b,d]pyran-1-ol in mice (i.v.) showed an MED at 10 Mg/kg for decrease in motor activity, thus indicating potential use as a tranquilizing agent.

The tranquilizing activity of 3-(3-oxo-1-octenyl)-6a,7,10,10a-tetrahydro-6,6,9-trimethyl-6H-dibenzo[b,d]pyran-1-ol was demonstrated in the rat motor activity test (Plotnikoff U.S. Pat. No. 3,755,584). At 10 mg/kg orally it decreased motor activity 39%, at 20 mg/kg it increased motor activity 48% and at 40 mg/kg it decreased motor activity 81%. The tranquilization activity of this compound was also demonstrated by suppressing mouse fighting behavior induced by footshock as determined by a modified Tedeschi procedure (J. Pharmacol. Exp. Therap., 125, 28–34, (1959). At 10 mg/kg per os there was an 80% reduction in agression after 30 minutes and a 79% reduction after 90 minutes while at 20 mg/kg there was a 96% reduction after 30 minutes and a 97% reduction after 90 minutes. In mice this compound has an MED of < 0.1 mg/kg i.v. for decrease in motor activity.

The tranquilizing activity of 3-(3-hydroxy-1-octenyl)-6a,7,10,10a-tetrahydro-6,6,9-trimethyl-6H-dibenzo[b,d]pyran-1-ol was also demonstrated in the rat motor activity test. At 10 mg/kg orally it increased motor activity 27%, at 20 mg/kg it decreased motor activity 44% and at 40 mg/kg it decreased motor activity 25%. The antagonism of this compound to methamphetamine-induced hyperactivity in rats (Plotnikoff U.S. Pat. No. 3,755,584) when administered orally was also measured and found to give a 7% reduction in activity at 10 mg/kg orally; a 3% reduction at 20 mg/kg; and a 37% reduction at 40 mg/kg, thus further demonstrating its tranquilizing activity. The compound in mice (i.v.) showed an MED at 2.0 mg/kg for decrease in motor activity.

The calming or tranquilizing activity of 3-(3-hydroxy-1-octenyl)-6a,7,10,10a-tetrahydro-6,6,9-trimethyl-6H-dibenzo[b,d]pyran-1-ol was further demonstrated in the mouse fighting test. At 10 mg/kg per os in mice it increased agression 2% in 30 minutes and after 90 minutes there was 0% change in agression from the control. At 20 mg/kg a 32% reduction in agression in 30 minutes was observed and after 90 minutes the reduction was 33% from the control.

3-(3-hydroxy-1-octenyl)-6a,7,10,10a-tetrahydro-6,6,9-trimethyl-6H-dibenzo[b,d]pyran-1-ol was found to have moderate antidepressent activity orally at 20 mg/kg in mice in the modified DOPA potentiation test (Everett, G. M., Proc. First Internat. Sympos. Antidepressant Drugs, Excerpta Med. Int. Cong. Ser. No. 122,1966).

1-acetoxy-3-(3-acetoxy-1-octenyl)-6a,7,10,10a-tetrahydro-6,6,9-trimethyl-6H-dibenzo[b,d]pyran was found to have an MED in mice of 1.0 mg/kg i.v. for decrease in motor activity.

The preset invention includes within its scope pharmaceutical compositions comprising, as an active ingredient, at least one of the compounds of formulas I, and VII to X, of this invention in association with a pharmaceutically acceptable carrier or diluent. The compounds of this invention exhibit both oral and parenteral activity and can be formulated in dosage forms for oral, parenteral or rectal administration.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate, and sweetening Liquid dosage flavoring agents. Tablets and pills can additionally be prepared with enteric coatings.

Liquiddosage forms for oral administration include pharmaceutically acceptable emulsions, solutions, suspensions, syrups and elixirs containing inert diluents commonly used in the art, such as water. Besides inert diluents, such compositions can also include adjuvants, such as wetting agents, emulsifying and suspending agents and sweetening, flavoring and perfuming agents.

Preparations according to this invention for parenteral administration include sterile aqueous or non-aqueous solutions, suspensions or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irridating the compositions, or by heating the compositions. They can also be manufactured in the form of sterile solid compositions which can be dissolved in sterile water, or some other sterile injectable medium immediately before use.

Compositions for rectal administration are suppositories which may contain in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration and on the duration of the treatment. Generally, dosage levels of between 0.1 to 40 mg/kg of body weight daily are administered to patients in need of tranquilization or relief from depression.

The following is an illustration of the pharmaceutical compositions which are a feature of this invention:

Tablet Composition

Tablets weighing 100 mg. and having the following composition are prepared by standard tableting procedures:

| Ingredient | Mg. |
|---|---|
| 3-(3-hydroxy-1-octenyl)-6a,7,10,10a-tetrahydro-6,6,9-trimethyl-6H-dibenzo[b,d]pyran-1-ol | 25 |
| Starch | 69 |
| Colloidal silica | 5 |
| Magnesium stearate | 1 |

The following examples are presented to further illustrate the invention.

EXAMPLE 1

3,5-Diacetoxybenzaldehyde

A total of 82.4 ml of acetic anhydride (89.8 g, 0.88 mole) was added in small portions to a stirring mixture of 61.7 g of 3,5-dihydroxybenzoic acid (0.4 mole) in 130 ml of pyridine. After the addition was complete, the reaction mixture was left stirring for 15 hours at ambient temperature. The pyridine was removed by evaporation in vacuo. The residue was taken up in $CH_2Cl_2$ and washed several times with 6N HCl and water and dried ($Na_2SO_4$). Removal of solvent under reduced pressure left 68.2 g (72%) of 3,5-diacetoxybenzoic acid which was used without further purification.

A stirring mixture of 68.2 g (0.29 mole) of 3,5-diacetoxybenzoic acid and 21 ml (0.29 mole) of thionyl chloride in 150 ml of dry benzene was heated in an oil bath at 80°-90° C. for 2 hours. After cooling the benzene was removed in vacuo to leave 3,5-diacetoxybenzoyl chloride as a tan, solid which was recrystallized from cyclohexane as colorless crystals, mp 87°-89° C., 61.8 g (83% yield).

A mixture of 61.8 g (0.24 mole) of 3,5-diacetoxybenzoyl chloride and 6 g of 5% palladium on $BaSO_4$ in 200 ml of dry xylene was efficiently stirred while bubbling in hydrogen gas. The reaction mixture was slowly heated to 115° C. in an oil bath and the heating was continued until the evolution of HCl gas ceased (approximately 5 hours). After cooling, the mixture was filtered and the xylene was removed in vacuo to leave 48 g (90%) of 3,5-diacetoxybenzaldehyde which was used without further purification in subsequent reactions.

EXAMPLE 2

1,3-Diacetoxy-5-(1,3-dithiolan-2-yl)benzene and 5-(1,3-Dithiolan-2-yl)resorcinol Dry hydrogen chloride was bubbled into a solution of 50.0 g (0.23 mole) of 3,5-diacetoxybenzaldehyde and 21.4 g (0.23 mole) of 1,2-ethanedithiol in 25 ml of ether until the solution became warm. After allowing the solution to stand at ambient temperature for 0.75 hour, the solvent was removed in vacuo and excess methanol was added. A solid of 1,3-diacetoxy-5-(1,3-dithiolan-2-yl)benzene (mp 94°–96° C.) was separated by filtration. It was resuspended in 100 ml of methanol and 21.7 g (0.23 mole) of potassium hydroxide pellets were added. On stirring the mixture at ambient temperature for 0.5 hour, the mixture became homogeneous. The solvent was removed in vacuo and the residue after acidification with 6N hydrochloric acid was extracted with ethyll acetate. The extract was washed with water until neutral, dried and evaporated in vacuo to leave 5-(1,3-dithiolan-2-yl)resorcinol as a gum (41.3 g, 84%) which was used without further purification in the subsequent reaction. The structure was confirmed by the infrared and nuclear magnetic resonance spectra.

EXAMPLE 3

3-(1,3-Dithiolan-2-yl)-6a,7,10,10a-tetrahydro-6,6,9-trimethyl-6H-dibenzo[b,d]pyran-1-ol To a solution of 41.3 g (0.193 mole) of 5-(1,3-dithiolan-2-yl)resorcinol in 500 ml of benzene was added 35.3 g (0.23 mole) of (+)-trans-p-mentha-2,8-dien-1-ol and 6.8 g (0.036 mole) of p-toluenesulfonic acid monohydrate. An additional 250 ml of benzene was added and the solution was refluxed using a water collector for 0.7 hour. After cooling, the mixture was washed with water, dried and evaporated to leave 65.2 g of a gum. Purification by column chromatography on magnesium silicate using benzene as the eluant gave 36.4 g (54%) of 3-(1,3-dithiolan-2-yl)-6a,7,10,10a-tetrahydro-6,6,9-trimethyl-6H-dibenzo[b,d]pyran-1-ol as a resinous material. The infrared and nuclear magnetic resonance spectra were in agreement with the proposed structure.

EXAMPLE 4

3-Formyl-6a,7,10,10a-tetrahydro-6,6,9-trimethyl-6H-dibenzo[b,d]pyran-1-ol

To a slurry of 28.16 g (0.13 mole) of mercuric oxide (red) in 200 ml of tetrahydrofuran was added 43.5 ml of water and 10.9 ml (0.09 mole) of boron trifluoride etherate. With vigorous stirring a solution of 17.5 g (0.05 mole) of 3-(1,3-dithiolan-2-yl)-6a,7,10,10a-tetrahydro-6,6,9-trimethyl-6H-dibenzo[b,d]pyran-1-ol in 100 ml of tetrahydrofuran was added dropwise. The color changed from bright red to a brownish-red. After stirring at ambient temperature for 1 hour, the mixture was filtered and excess ether was added to the filtrate. The solution was washed consecutively with water, 5% sodium bicarbonate, again with water, dried and evaporated to leave 12.1 g of a gum. It was purified by chromatography on 500 g of magnesium silicate and eluted with chlorofrom to yield 7.6 g (56%) of 3-formyl-6a,7,10,10a-tetrahydro-6,6,9-trimethyl-6H-dibenzo[b,d]pyran-1-ol. Glc showed it to be >90% pure; the infrared and nuclear magnetic resonance spectra confirmed the proposed structure.

EXAMPLE 5

3-(3Oxo-1-octenyl)-6a,7,10,10a-tetrahydro-6,6,9-trimethyl-6H-dibenzo[b,d]pyran-1-ol A mixture of 7.55 g (0.028 mole) of 3-formyl-6a,7,10,10a-tetrahydro-6,6,9-trimethyl-6H-dibenzo[b,d]pyran-1-ol and 6.16 g (0.028 mole) of dimethyl(2-oxoheptyl)phosphonate (Aldrich) was added dropwise to a slurry of 1.34 g (0.056 mole) of sodium hydride (57% oil dispersion) in 1,2-dimethoxyethane. After the addition was complete, the mixture was stirred at 85° C. for 1 hour. After cooling, the excess sodium hydride was decomposed by the slow addition of a 1:1 ether/methanol mixture followed by excess water. The aqueous phase was extracted three times with ether and the ethereal solution was dried and concentrated in vacuo to give 8.1 g of a gum. Purification by chromatography on 300 g of magnesium silicate and elution with 1:4 ethyl acetate/hexane furnished 5.6 g (56%) of 3-(3-oxo-1-octenyl)-6a,7,10,10a-tetrahydro-6,6,9-trimethyl-6H-dibenzo[b,d]pyran-1-ol as a tan solid, mp 119°–122 C. The proposed structure was confirmed by the infrared and nuclear magnetic resonance spectra.

Anal. Calcd. for $C_{24}H_{32}O_2$: C, 78.22; H, 8.75. Found: C, 78.29; H 8.90.

EXAMPLE 6

3-(3-Hydroxy-1-octenyl)-6a,7,10,10a-tetrahydro-6,6,9-trimethyl-6H-dibenzo[b,d]pyran-1-ol A solution of 4.6 g (0.013 mole) of 3-(3-oxo-1-octenyl)-6a,7,10,10a-tetrahydro-6,6,9-trimethyl-6H-dibenzo[b,d]pyran-1-ol in ether was added dropwise to a slurry of 0.34 g (0.009 mole) of lithium aluminum hydride in ether. After the addition was complete, the mixture was stirred at room temperature for 1 hour and decomposed by the successive addition of water, 15% sodium hydroxide, and water. The filtrate was concentrated in vacuo to give 3.8 g of a gum which was purified by chromatography on 300 g of magnesium silicate and eluted with graded mixtures of ether (25 to 50%)/petroleum ether. Following chromatography, there was obtained 2.8 g (57%) of 3-(3-hydroxy-1-octenyl)-6a,7,10,10a-tetrahydro-6,6,9-trimethyl-6H-dibenzo[b,d]pyran-1-ol as an amber glossy solid. The infrared and nuclear magnetic resonance spectra were in agreement with the proposed structure.

Anal. Calcd. for $C_{24}H_{34}O_3$: C, 77.8; H, 9.25. Found: C, 77.64; H, 9.12.

EXAMPLE 7

1-Acetoxy-3-(3-acetoxy-1-octenyl)-6a,7,10,10a-tetrahydro-6,6,9-trimethyl-6H-dibenzo[b,d]pyran A solution of 1.75 g (0.0047 mole) of 3-(3-hydroxy-1-octenyl)-6a,7,10,10a-tetrahydro-6,6,9-trimethyl-6H-dibenzo[b,d]pyran-1-ol and 1.23 g (0.012 mole) of acetic anhydride in 10 ml of pyridine was warmed on the steam bath. After 3.5 hours, the pyridine was removed in vacuo and the residue was dissolved in ether. The ethereal solution was washed with dilute hydrochloric acid followed by water. After drying, it was evaporated to leave 2.1 g (97%) of 1-acetoxy-3-(3-acetoxy-1-octenyl)-6a,7,10,10a-tetrahydro-6,6,9-trimethyl-6H-dibenzo[b,d]pyran as a gum which was pure by tlc (benzene). The infrared and nuclear magnetic resonance spectra were in agreement with the proposed structure.

EXAMPLE 8

3-(3-Hydroxy-3-methyl-1-octenyl)-6a,7,10,10a-tetrahydro-6,6,9-trimethyl-6H-dibenzo[b,d]pyran-1-ol A solution of 1.0 g (0.0028 mole) of 3-(3-oxo-1-octenyl)-6a,7,10,10a-tetrahydro-6,6,9-trimethyl-6H-dibenzo[b,d]pyran-1-ol in diethyl ether was added dropwise to a solution of methyl magnesium bromide in ether prepared by bubbling methyl bromide into 0.78 g (0.032 mole) of magnesium. After the addition was complete, the mixture was refluxed for 3 hours and then decomposed by the careful addition of a mixture of methanol/diethyl ethr followed by dilute acid. The ethereal layer was separated and washed consecutively with water, 5% sodium bicarbonate and again water. It was dried and evaporated to leave 0.95 g of a gum which was chromatographed on magnesium silicate and eluted with graded mixtures of ether/petroleum ether. This furnished 0.28 g of 3-(3-hydroxy-3-methyl-1-octenyl)-6a,7,10,10a-tetrahydro-6,6,9-trimethyl-6H-dibenzo[b,d]pyran-1-ol as a resinous material. The infrared and nuclear magnetic resonance spectra were consistent with the structure of the desired hydroxy compound.

The foregoing detailed description has been given for clearness of understanding only, and no unnecessary limitations should be understood therefrom, as modifications will be obvious to those skilled in the art.

What is claimed is:

1. A compound of the formula

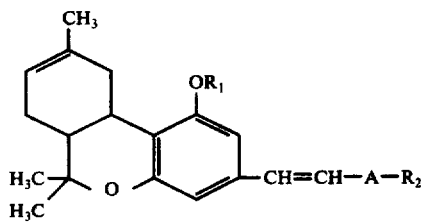

wherein $R_1$ is hydrogen or lower alkanoyl, $R_2$ is a $C_1$ to $C_{20}$ alkyl, aryl-lower alkyl or cycloalkyl-lower alkyl, A represents

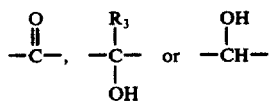

when $R_1$ is hydrogen and $R_3$ is lower alkyl, and A is

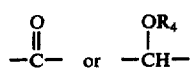

when $R_1$ is lower alkanoyl and $R_4$ is the same lower alkanoyl represented by $R_1$.

2. A compound according to claim 1 in which $R_1$ is hydrogen, $R_2$ is a $C_1$ to $C_{20}$-alkyl and A is

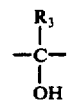

in which $R_3$ is lower alkyl.

3. A compound according to claim 2 in which the lower alkyl represented by $R_3$ is methyl or ethyl.

4. A compound according to claim 1 in which $R_1$ is hydrogen, $R_2$ is a $C_1$ to $C_{20}$-alkyl and A is

5. A compound according to claim 1 in which A is

$R_1$ is lower alkanoyl and $R_2$ is a $C_1$ to $C_{20}$-alkyl.

6. A compound according to claim 1 in which A is

$R_1$ and $R_4$ represent the same lower alkanoyl and $R_2$ is a $C_1$ to $C_{20}$-alkyl.

7. A compound according to claim 4 named 3-(3-hydroxy-1-octenyl)-6a,7,10,10a-tetrahydro-6,6,9-trimethyl-6H-dibenzo[b,d]pyran-1-ol.

8. A compound according to claim 6 named 1-acetoxy-3-(3-acetoxy-1-octenyl)-6a,7,10,10a-tetrahydro-6,6,9-trimethyl-6H-dibenzo[b,d]pyran.

9. A compound according to claim 3 named 3-(3-hydroxy-3-methyl-1-octenyl)-6a,7,10,10a-tetrahydro-6,6,9-trimethyl-6H-dibenzo[b,d]pyran-1-ol.

10. A compound of the formula

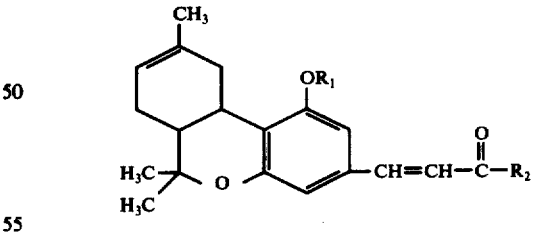

wherein $R_1$ is hydrogen or lower alkanoyl and $R_2$ is a $C_1$ to $C_{20}$-alkyl.

11. A compound according to claim 10 in which $R_1$ is hydrogen.

12. A compound according to claim 10 named 3-(3-oxo-1-octenyl)-6a,7,10,10a-tetrahydro-6,6,9-trimethyl-6H-dibenzo[b,d]pyran-1-ol.